United States Patent [19]
Shore et al.

[11] 3,934,674
[45] Jan. 27, 1976

[54] ACOUSTIC HEADSETS

[76] Inventors: Sidney X. Shore, 29 Wren Drive, Roslyn, N.Y. 11576; Paul S. Martin, 189-54 43rd Road, Flushing, N.Y. 11358

[22] Filed: Aug. 29, 1974

[21] Appl. No.: 501,688

[52] U.S. Cl. ............... 181/135; 181/131; 179/1 ST
[51] Int. Cl.² ............................................ A61B 7/02
[58] Field of Search .......... 181/135, 126, 129, 130, 181/131; 179/1 ST, 156 R, 182 R

[56] References Cited
UNITED STATES PATENTS

| | | | |
|---|---|---|---|
| 2,142,407 | 1/1939 | Norton et al. | 181/135 |
| 3,623,571 | 11/1971 | French | 181/135 |
| 3,730,290 | 5/1973 | Scanlon | 181/135 |
| 3,776,362 | 12/1973 | Rice | 181/135 |

*Primary Examiner*—Stephen J. Tomsky

[57] ABSTRACT

Acoustic headsets, especially for transmitting sound from stereo transducers to the listener's ears, include two tubes, earpieces at first ends of the tubes, and a frame for constraining the tubes into a convenient U-shape near the wearer's face. The headset has resilient arms at the sides of the U-shaped frame, and more particularly, the arms have resilient inner and outer strips along respective ones of said tubes, facing toward and away from the center line of the frame. The strips are interconnected at their extremities, and in the exemplary embodiment the inner and outer strips of each arm are interconnected by a bridge between the extremities of the strips.

5 Claims, 3 Drawing Figures

ACOUSTIC HEADSETS

FIELD OF THE INVENTION

This invention relates to acoustic headsets, for transmitting sound from a transducer or a pair of transducers along tubes to a listener's ears.

BACKGROUND OF THE INVENTION

A widely used type of acoustic headset includes earpieces carried at first ends of a pair of sound-transmitting tubes, and a one-piece frame to hold the earpieces in place against the wearer's outer ears and to shape the tubes conveniently alongside the wearer's face. In the known headsets, there are two rigid arms in the form of elongated channels for supporting the earpieces, the arms being carried on resilient portions of the frame. The arms move angularly apart and then toward each other when the headset is being put on, thus fitting different persons differently. Moreover, the resilient support for the arms which is primarily intended to provide gentle bias of the earpieces against the ears must additionally be firm enough to bear the weight of the arms, a weight that changes when the wearer moves his head from time to time. Slight changes in attitude and in pressure of the earpieces can develop discomfort in some individuals where the listening period is prolonged.

SUMMARY OF THE INVENTION

The disclosed embodiment of the invention involves a one-piece U-shaped frame for the acoustic tubes of an improved headset, wherein the arms of the U-shaped frame provide the requisite resilience. More particularly, each of the arms includes an inner strip and an outer strip along the tube, facing toward and away from the center-line of the frame between the arms, and the strips are connected at their extremities. The in-turned portions of the arms which direct the earpieces against the wearer's outer ears are small and light parts, carried by the resilient arms and, as will be seen, the outer strips of each arm, acting against the constraint of the inner strip, has a tendency to maintain reasonably constant the attitude of the in-turned frame portions despite use of the headsets by various people. These features and others promote improved comfort for the wearer.

The nature of the invention and its further novel features and advantages will be better appreciated from the following detailed description of an illustrative embodiment, which is shown in the accompanying drawings. In the drawings.

Figure 1:
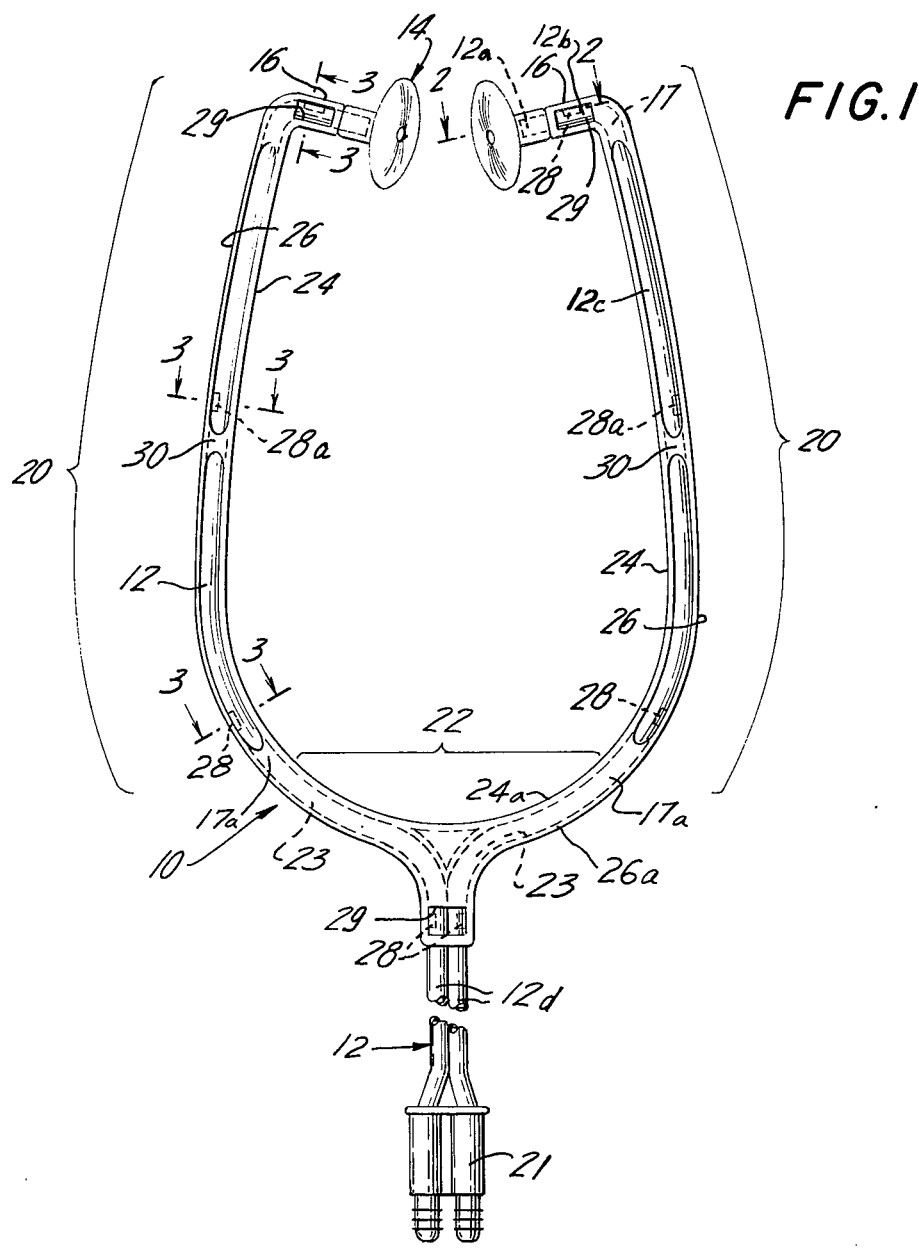
FIG. 1 is a front view drawn to reduced scale of an acoustic headset incorporating the features of the invention.

The acoustic stereo headset in the drawings has a frame 10 for holding the flexible acoustic or sound-transmitting tubes 12 in the shape shown. The frame is molded of any suitable plastic, in one piece. Earpieces 14 are of readily deformable material. Earpieces 14 are supported on first end portions 12a of tubes 12 projecting from the in-turned upper end portions 16 of the frame which contain second portions 12b of the tubes.

Figure 2:
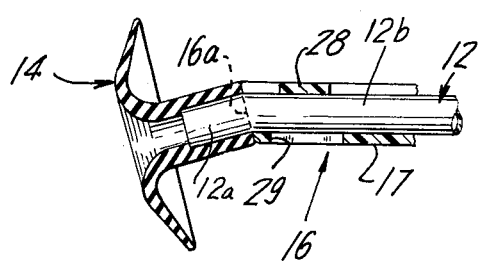
FIG. 2 is an enlarged framentary cross-section of an in-turned frame portion and an earpiece as viewed at the plane 2—2 in FIG. 1.

As seen in FIG. 2, end portions 16 of the frame have slant ends 16a that directs the earpieces at a slight forward angle relative to the front surface 17 of the frame (the lower surface 17 of in-turned frame portion 16 as shown in FIG. 2). This angle is for aiming the earpieces conveniently into the external ears of the wearer.

Frame 10 includes two flexible arms 20 extending from a rigid center portion 22. Tubes 12 extend to a fitting or plug-in terminal 21 for a receptacle containing two chambers and a pair of stereo sound-producing transducers (not shown). Between fitting 21 and portion 22 of the frame, the two tubes 12 are united where they are tangent to each other, and they extend (as shown) separately in frame 10. Rigid central portion 22 and in-turned end portions 16 of the frame are of known construction. Heretofore most of the length of the arms has been rigid in one known form of comparable headset, while in another known form of headset the entire length of each arm has been rigid and the arms are connected by a resilient central section of the frame.

Figure 3:
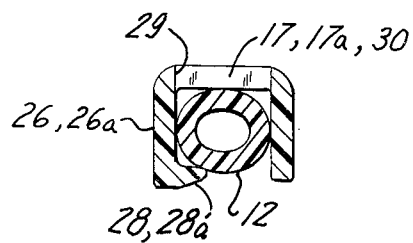
FIG. 3 is an enlarged cross-section of the headset of FIG. 1 at any of the planes 3—3 in FIG. 1.

Center portion 22 provides two channels 23 for containing third portions 12c of acoustic tubes 12 extending from tube portions 12b in the upper end portions of the frame to further tube portions 12d. Arms 20 comprise inner strips 24 and outer strips 26, which guide and confine tubes 12, facing toward and away from the center-line of the frame between the arms. Channels 23 are defined by front wall 17a and side walls 24a and 26a extending from strips 24 and 26, respectively. A bridge 30 of each arm interconnects strips 24 and 26 of that arm at the front of the frame as viewed in FIG. 1. Plural detents 28 and 28a (FIGS. 1, 2 and 3) restrain the tubes 12 in the position described. Detents 28 and 28a are provided at suitable places, such as those represented at the three section lines 3—3 in FIG. 1. Each detent 28 extends from a side wall of a tube-containing channel in portions 16 and 22 of the head-set at the back of the head-set (FIG. 3) partway across the channel, and each detent 28a extends from a tube-guiding strip 26 in each of the arms of the head-set, at the back of the head-set and only partway across the space between strips 24 and 26. (Windows 29 have no purpose in the use of the headset, but result from penetration by parts of the mold involved in shaping detents 28.) At their upper ends, the separation or spacing of strips 24 and 26 is fixed by front surfaces 17 of end portions 16 of the frame. This spacing is suitable for snugly receiving the tubes 12. At the lower ends of arms 20, the separation of strips 24 and 26 is fixed by center portion 22 at the same tube-receiving space. Bridges 30 fix the same spacing between strips 24 and 26 about midway along their lengths. Strips 24 and 26 inherently tend to spread apart when the arms are spread in use, and the restraint afforded by bridge 30 improves the appearance of the head-set and enables strips 24 and 26 to guide and confine the acoustic tubes. Detents 28a are located close to bridges 30 where spreading of the strips is prevented, thereby assuring the efficacy of these detents.

When the headset is not in use, arms 20 hold earpieces 14 at a separation much less than the ear-to-ear dimension of a person's head. The arms 20 of the frame are highly resilient, so that the earpieces can be spread far apart in putting on the headset, and then the resilience of the arms presses the earpieces gently but dependably into the outer ears of the wearer.

When arms 20 are moved farther apart from each other than they are in the at-rest state of the headset illustrated there is a tendency of outer strips 26 to bow away from inner strips 24. Bridges 30 serve to restrict this action, for improved appearance and for confining these strips against such separation as would allow the tubes 12 to become free of detents 28a. Thus detents 28a and bridges 30 assure retention of tubes 12 between strips 24 and 26.

The disposition of in-turned end portions 16 of the frame is designed to direct the earpieces properly for comfortable and effective cooperation with the wearer's ears. As arms 20 are pulled apart for putting on the headset, they move through appreciable angles, and while such separation is taken into account in designing the angle of in-turned portions 16, the angle of separation of the arms 20 varies among different users, depending on their head sizes. However, strips 24 and 26 have an action that tends to compensate for the angular motions of the arms. Outer strips 26 have a tendency of tilting frame portions 16 slightly inward toward frame part 22 while strips 24 exert restraint and cooperate in this action.

The entire headset is of a design that virtually eliminates risk of hair of the wearer becoming entangled or trapped. This is a consideration of practical importance and yet it is satisfied in what is otherwise an economical and effective form of headset.

The nature of the invention in its various aspects is represented in the illustrative embodiment shown in the accompanying drawings and described in detail above. However, that embodiment is susceptible of modification in various details by those skilled in the art and therefore the invention should be construed broadly in accordance with its full spirit and scope.

What is claimed is:

1. An acoustic headset having a pair of sound-transmitting tubes, a pair of earpieces carried by respective first end portions of said tubes, and a generally U-shaped frame having in-turned end portions containing and directing second portions of said tubes adjacent first end portions thereof, said frame further including resilient arms containing third portions of said tubes extending from said in-turned end portions thereof, said frame further including a central portion carrying said arms, and a plug-in terminal, said tubes each including a further length extending to said plug-in terminal from said third portions thereof, respectively, said arms having inner and outer strips separated from each other along their entire lengths except for localized interconnections at widely spaced locations including interconnections at their extremities, and said inner and outer strips extending along said third portions of said tubes at the sides thereof facing toward and away from the center-line of the U-shaped frame.

2. An acoustic headset in accordance with claim 1, wherein a said localized interconnection forms a bridge in each of said arms between the extremities thereof at one side of the associated tube, and including a detent on at least one of said strips near said bridge at the side of said associated tube opposite said bridge.

3. An acoustic headset in accordance with claim 1, wherein said central portion of the frame is essentially rigid and includes channel means retentively containing portions of said further lengths of said tubes.

4. An acoustic headset in accordance with claim 1, wherein said in-turned end portions and said central portion of said frame comprise channel formations containing portions of said tubes and include detents for restraining said tube portions in said channel formations.

5. An acoustic headset in accordance with claim 4, wherein a said interconnection forms a bridge in each of said arms connecting said inner and outer strips between the extremities thereof at one side of the related tube and including a tube-retaining detent at the opposite side of said tube near each last-named interconnection.

* * * * *